(12) United States Patent
Sierra

(10) Patent No.: US 9,021,875 B2
(45) Date of Patent: May 5, 2015

(54) BI-DIRECTIONAL FLOW AND DISTRIBUTED TEMPERATURE SENSING IN SUBTERRANEAN WELLS

(75) Inventor: Jose Sierra, Mexico City (MX)

(73) Assignee: Halliburton Energy Services, Inc., Houston, TX (US)

(*) Notice: Subject to any disclaimer, the term of this patent is extended or adjusted under 35 U.S.C. 154(b) by 843 days.

(21) Appl. No.: 13/133,490

(22) PCT Filed: Feb. 12, 2010

(86) PCT No.: PCT/US2010/024100
§ 371 (c)(1),
(2), (4) Date: Jun. 8, 2011

(87) PCT Pub. No.: WO2010/093920
PCT Pub. Date: Aug. 19, 2010

(65) Prior Publication Data
US 2011/0232377 A1  Sep. 29, 2011

Related U.S. Application Data

(60) Provisional application No. 61/152,568, filed on Feb. 13, 2009.

(51) Int. Cl.
E21B 47/10 (2012.01)
G01N 33/28 (2006.01)
E21B 49/10 (2006.01)

(52) U.S. Cl.
CPC ........ E21B 47/1005 (2013.01); *G01N 33/2823* (2013.01); *E21B 49/10* (2013.01)

(58) Field of Classification Search
CPC ......... E21B 47/10; E21B 49/10; E21B 47/00; E21B 2049/085; E21B 49/08; E21B 49/081; G01N 33/2823

USPC ....................................................... 73/152.18
See application file for complete search history.

(56) References Cited

U.S. PATENT DOCUMENTS 7,475,724 B2    1/2009  Pribnow et al.
7,731,421 B2 *  6/2010  Hadley et al. ................. 374/136
(Continued)

FOREIGN PATENT DOCUMENTS

WO    WO 04001356 A2 * 12/2003
WO    WO 2004076815 A1 *  9/2004 .............. E21B 49/00

OTHER PUBLICATIONS

International Search Report with Written Opinion issued Aug. 19, 2010 for International Patent Application No. PCT/US2010/024100, 14 pages.

(Continued)

*Primary Examiner* — Hezron E Williams
*Assistant Examiner* — Rodney T Frank
(74) *Attorney, Agent, or Firm* — Smith IP Services, P.C.

(57) ABSTRACT

A method of determining characteristics of fluids flowed between a wellbore and multiple zones intersected by the wellbore can include measuring a first distributed temperature profile of the fluids along the wellbore while the fluids flow in one direction through the wellbore, and measuring a second distributed temperature profile of the fluids along the wellbore while the fluids flow in an opposite direction through the wellbore. Another method can include flowing the fluids in a first direction through an annulus formed between tubular strings in the wellbore, measuring a first distributed temperature profile of the fluids while flowing the fluids in the first direction, flowing the fluids in a second, opposite direction through the annulus, and measuring a second distributed temperature profile of the fluids along the wellbore while flowing the fluids flow in the second direction.

16 Claims, 4 Drawing Sheets

(56) References Cited

U.S. PATENT DOCUMENTS

2005/0024231 A1* 2/2005 Fincher et al. ............ 340/854.4
2007/0234788 A1 10/2007 Glasbergen
2008/0314142 A1* 12/2008 Davies ........................... 73/295
2009/0173494 A1 7/2009 Tarvin et al.

OTHER PUBLICATIONS

Welldynamics; "iFlow", New concepts for Fiber Optics DTS Gas Flow Profiling, dated Feb. 2008, 40 pages.

* cited by examiner

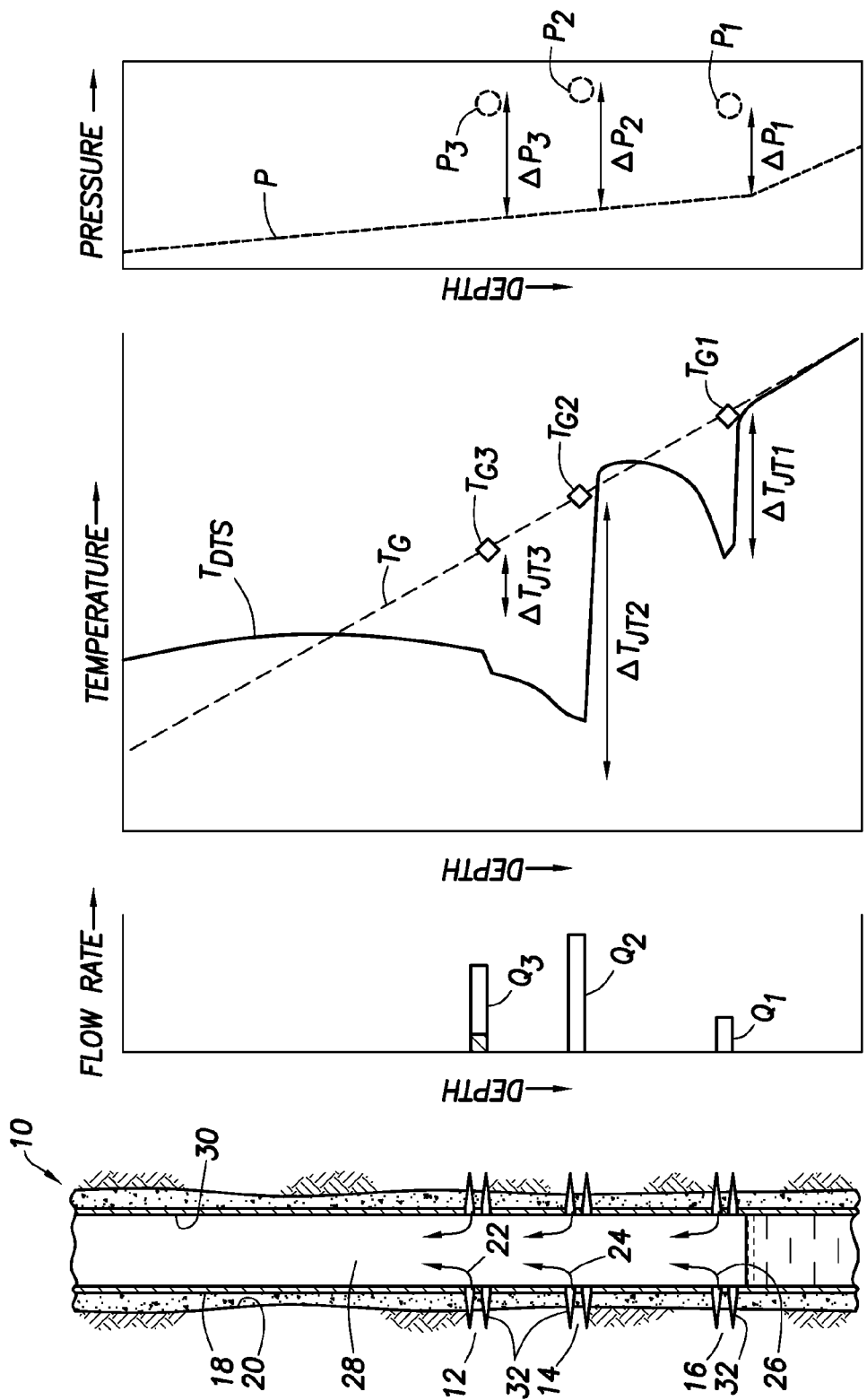

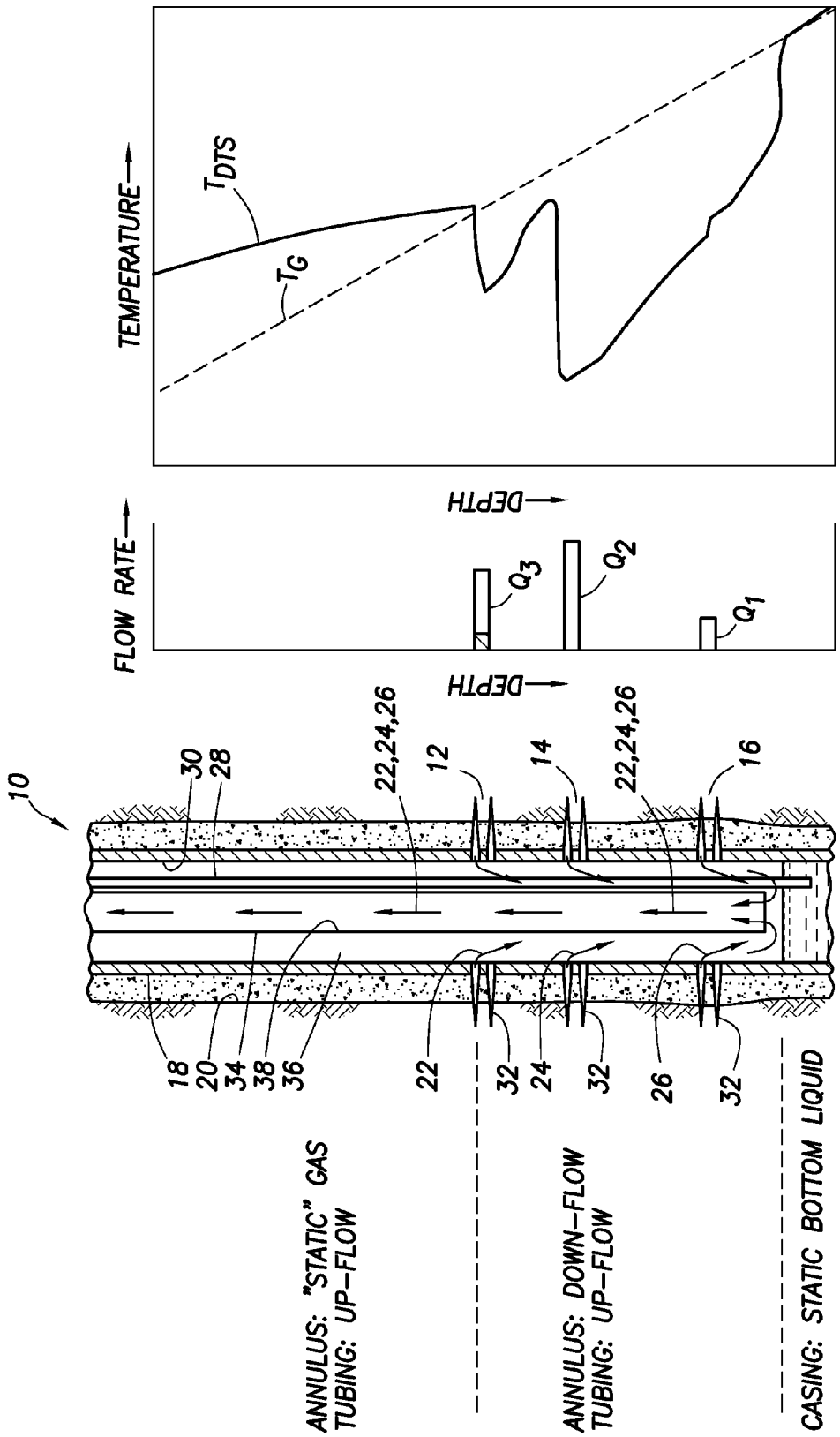

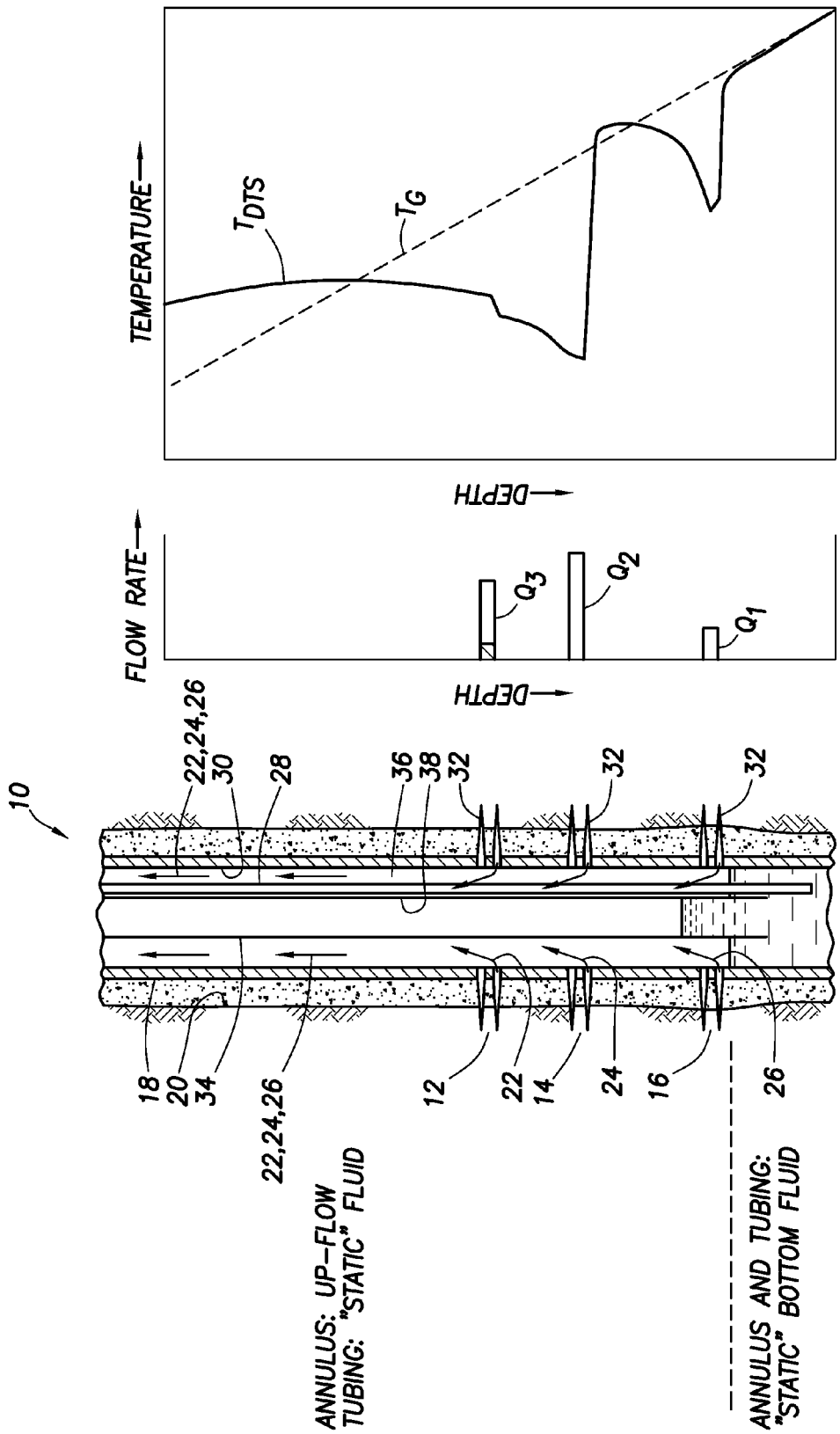

BI-DIRECTIONAL FLOW AND DISTRIBUTED TEMPERATURE SENSING IN SUBTERRANEAN WELLS

TECHNICAL FIELD

The present disclosure relates generally to equipment utilized and operations performed in conjunction with subterranean wells and, in an embodiment described herein, more particularly provides for bi-directional flow and distributed temperature sensing in subterranean wells.

BACKGROUND

Distributed temperature sensing in subterranean wells has been performed in the past using optical fiber sensors. Such optical fiber sensors, and distributed temperature measurements made using the sensors, have also been used to determine where flow from a formation enters a wellbore. However, past methods of measuring flow into the wellbore have not been completely satisfactory, particularly in those circumstances in which fluids enter the wellbore from multiple zones, with the fluids being comingled in the wellbore.

SUMMARY

In carrying out the principles of the present disclosure, a well system and associated methods are provided which bring improvements to the art of determining characteristics of fluids flowed between a wellbore and zones intersected by the wellbore. One example is described below in which the fluids flow into the wellbore, and the temperature of the fluids is measured by a distributed temperature sensing system. Another example is described below in which the fluids are flowed in opposite directions through the wellbore when the temperature measurements are made.

In one aspect, a method of determining characteristics of fluids flowed between a wellbore and multiple zones intersected by the wellbore is provided to the art by this disclosure. The method includes the steps of measuring a first distributed temperature profile of the fluids along the wellbore while the fluids flow in one direction through the wellbore; and measuring a second distributed temperature profile of the fluids along the wellbore while the fluids flow in an opposite direction through the wellbore.

In another aspect, a method of determining characteristics of fluids flowed between a wellbore and multiple zones intersected by the wellbore is provided which includes the steps of: flowing the fluids in one direction through an annulus formed between tubular strings in the wellbore, measuring a first distributed temperature profile of the fluids during the step of flowing the fluids in the one direction, flowing the fluids in an opposite direction through the annulus, and measuring a second distributed temperature profile of the fluids along the wellbore during the step of flowing the fluids in the opposite direction.

These and other features, advantages and benefits will become apparent to one of ordinary skill in the art upon careful consideration of the detailed description of representative embodiments of the disclosure hereinbelow and the accompanying drawings, in which similar elements are indicated in the various figures using the same reference numbers.

BRIEF DESCRIPTION OF THE DRAWINGS

FIG. 1A is a schematic cross-sectional view of a well system and associated method which can embody principles of the present disclosure.

FIG. 1B is a graph of flow rate versus depth along a wellbore in the system and method of FIG. 1A.

FIG. 1C is a graph of temperature versus depth along the wellbore in the system and method of FIG. 1A.

FIG. 1D is a graph of pressure versus depth along the wellbore in the system and method of FIG. 1A.

FIG. 2A is a schematic cross-sectional view of another configuration of the well system and method.

FIG. 2B is a graph of flow rate versus depth along a wellbore in the system and method of FIG. 2A.

FIG. 2C is a graph of temperature versus depth along the wellbore in the system and method of FIG. 2A.

FIG. 3A is a schematic cross-sectional view of yet another configuration of the well system and method.

FIG. 3B is a graph of flow rate versus depth along a wellbore in the system and method of FIG. 3A.

FIG. 3C is a graph of temperature versus depth along the wellbore in the system and method of FIG. 3A.

DETAILED DESCRIPTION

Figure 4B:
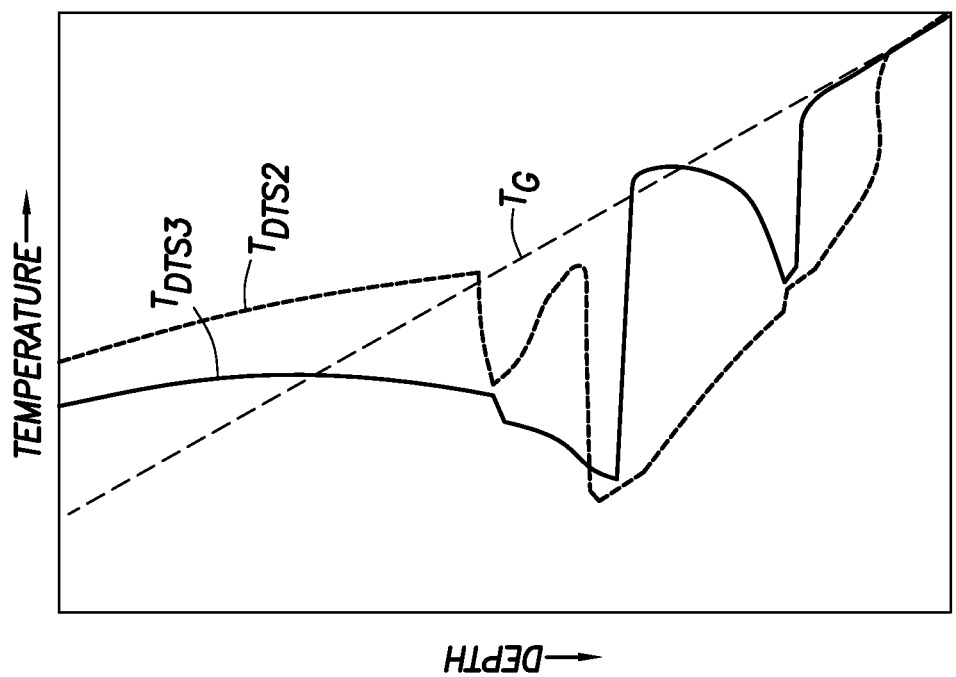
FIG. 4B is a graph of temperature versus depth along the wellbore in the system and method of FIGS. 2A & 3A.
Figure 4A:
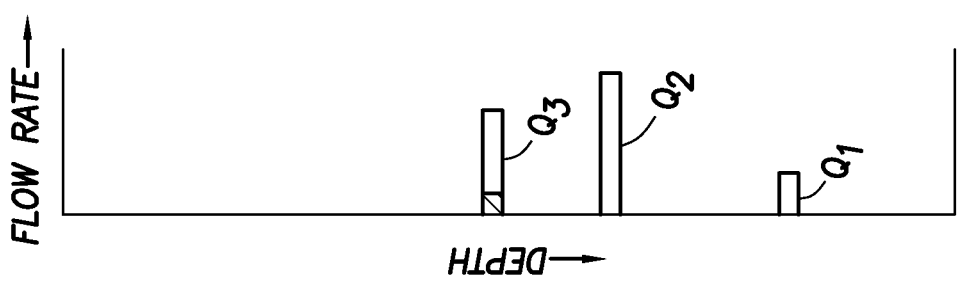
FIG. 4A is a graph of flow rate versus depth along a wellbore in the system and method of FIGS. 2A & 3A.

Representatively illustrated in FIG. 1A is a well system 10 which can embody principles of the present disclosure. In the example of FIG. 1A, the principles of this disclosure can be used to improve the quality of flow profile analyses derived from distributed temperature sensing (DTS) measurements in a flowing well and in a permanent monitoring application.

In other examples, the well could have other flow regimes, DTS sensors could be installed temporarily, in addition to, or as opposed to being installed permanently, etc. Thus, it should be clearly understood that the system 10 as depicted in FIG. 1A is merely one example of a useful application of this disclosure's principles, and those principles are not limited in any way to the details of the system 10 as shown in FIG. 1A or as described herein.

As is well known to those skilled in the art, DTS is performed using an optical waveguide (such as an optical fiber, optical ribbon, etc.), and the optical waveguide itself comprises a temperature sensor. Light is transmitted through the optical waveguide, and light reflected back through the optical waveguide provides an indication of the temperature along the optical waveguide.

Optical time domain reflectometry (OTDR) is used to determine the locations along the waveguide from which the light is reflected. Characteristics of the reflected light (e.g., intensity of Raman backscattering, wavelength of Brillouin backscattering, etc.) provide indications of the temperature of the optical waveguide at each location. The techniques used for DTS are well-known to those skilled in the art, and so they are not described further herein.

In the example of FIG. 1A, it is desired to determine the rate of flow of oil, gas and water from each zone 12, 14, 16 in a multi-zone well completion. The well is completed with a tubular string 18 (such as casing, liner, etc.) cemented in a wellbore 20.

Fluid 22, 24, 26 enters the wellbore 20 from the respective zones 12, 14, 16, and flows to the surface via the tubular string 18. The fluids 22, 24, 26 combine in the tubular string 18. In other examples, another tubular string (such as, a production tubing string, a velocity string, etc.) could be used to flow the fluids 22, 24, 26 to the surface, the zones 12, 14, 16 could be isolated from each other using packers, the wellbore 20 could be open hole or uncased, etc.

In the example of FIG. 1A, the fluids 22, 24, 26 can each include gas and/or liquid fluids. It is desired to determine the relative flow rate of each type of fluid from each of the zones 12, 14, 16 using DTS measurements acquired with an optical waveguide 28 installed in the well.

As depicted in FIG. 1A, the optical waveguide 28 extends longitudinally within an interior flow passage 30 of the tubular string 18, but in other examples, the optical waveguide could be external to the tubular string, incorporated into a sidewall of the tubular string, or otherwise positioned in the well. Other measurements (such as pressure measurements) may be made using the optical waveguide 28 or other sensors.

It is contemplated that the types of completions that the principles of this disclosure are most applicable to are velocity string completions and more complex completions, including intelligent completions, with isolation between zones, and where produced fluid can be selectively flowed either up the annulus or up the production tubing.

DTS measurements are used to periodically determine the temperature along the length of the wellbore 20. When fluid is not flowing through the wellbore 20, the temperature measured by the optical waveguide 28 would be the geothermal temperature $T_G$.

When the fluids 22, 24, 26 are flowing into the wellbore 20 via perforations 32, the flowing fluid temperature is measured by the optical waveguide 28. The variance from $T_G$ due to the temperature of fluid 22, 24, 26 flowing from each zone 12, 14, 16 (which is different from $T_G$) will be apparent on a graph of temperature versus depth along the wellbore 20.

If the fluids 22, 24, 26 are compressible (e.g., if the fluid is mostly or partially gas), then as it flows into the wellbore 20 (a region of reduced pressure relative to the respective zones 12, 14, 16), the reduction in pressure will result in a reduction in temperature of the fluid. This is due to what is commonly known as the Joule-Thomson effect.

The Joule-Thomson effect describes a change in temperature of a thermally insulated gas when it is forced through a small hole (such as the perforations 32) or a porous material (such as the formation rock of the zones 12, 14, 16). This is also known as the Joule-Kelvin effect. For typical well fluids, temperatures and pressures, a reduction in temperature of fluid would generally accompany a reduction in pressure of the fluid.

The DTS measurement of temperature of a flowing fluid at a particular location will indicate a difference in temperature of that fluid from the geothermal temperature $T_G$. The temperature difference will be due to both the Joule-Thomson effect, and temperature changes due to the bulk flowing fluid temperature.

As depicted in FIG. 1B, fluids 22, 24, 26 are produced from zones 12, 14, 16 at respective flow rates Q1, Q2 and Q3. In the FIG. 1B graph, the vertical axis represents depth along the wellbore 20 (with depth increasing in a downward direction), and the horizontal axis represents flow rate (with flow rate increasing to the right).

The relative flow rates Q1, Q2, Q3 are represented by bars in FIG. 1B. As illustrated by the hatched portion of the Q3 bar, some water is being produced from the uppermost zone 12. The unhatched portions of the Q1, Q2 and Q3 bars represent production of gas.

In FIG. 1C, a graph of temperature versus depth is representatively illustrated. In the FIG. 1C graph, the vertical axis represents depth along the wellbore 20 (with depth increasing in a downward direction), and the horizontal axis represents temperature (with temperature increasing to the right).

The geothermal temperature $T_G$ profile is depicted in FIG. 1C, as is the distributed temperature $T_{DTS}$ profile as measured by the optical waveguide 28 and its associated DTS system. Note that, with the fluids 22, 24, 26 flowing into the wellbore 20 as depicted in FIG. 1A, the DTS measured temperature $T_{DTS}$ deviates from the geothermal temperature $T_G$ at and above the zones 12, 14, 16. The temperature difference from $T_G$ ($T_{DTS}-T_G$) is due both to the Joule Thomson effect ($\Delta T_{JT}$) at a particular zone, and to the flowing temperature of fluid from any other zones below a particular zone.

$\Delta T_{JT1}$ (the Joule-Thomson temperature difference), and $Q_1$ at the lowest zone 16 can be readily calculated from pressure measurements and DTS temperature measurements along the wellbore 20, using analytical methods.

$$JTC = [\partial T/\partial P]_H \qquad (1)$$

wherein JTC is the Joule-Thomson coefficient for a real fluid, T is temperature, P is pressure and H is a particular enthalpy.

$$\Delta T_{JTn} = T_{Gn} - T_{SFn} \qquad (2)$$

wherein $\Delta T_{JTn}$ is the temperature difference due to the Joule-Thomson effect for fluid flowing from a particular zone n, $T_{Gn}$ is the geothermal temperature in a particular zone n, and $T_{SFn}$ is the measured DTS temperature, plus any temperature effect due to any other fluids comingled in the wellbore 20 with the fluid flowing from the zone n. Note that, for the lowermost zone 16, the entire temperature difference ($T_{DTS}-T_G$) is due to the Joule-Thomson effect $\Delta T_{JT1}$ since no other fluids are comingled with the fluid 26 at the location where the fluid 26 flows into the wellbore 20.

$$\Delta T_{JTn} = \Delta P_n * JTC_{gas\ n} \qquad (3)$$

$$\Delta T_{JTn} = \Delta P_n * JTC_{mix\ n} \qquad (4)$$

$$\Delta P_n \cong \Delta T_{JTn} / JTC_{gas\ n} \qquad (5)$$

wherein $\Delta P_n$ is the pressure difference between a zone n and the wellbore 20 at the location where fluid flows from the zone into the wellbore, $JTC_{gas\ n}$ is the Joules-Thomson coefficient for gas in a zone n, and $JTC_{mix\ n}$ is the Joules-Thomson coefficient for mixture of gas and liquid in a zone n.

$\Delta T_{JT}$ and Q can be calculated at each upper zone 12, 14, based on the flow rate Q from the zones below, and the DTS measurements above the zone. Using $\Delta T_{JT}$, the expected temperature change due to the temperature of fluids flowing from zones below and other known data about the fluids (i.e., density, heat capacity), the flow rate of oil, water and gas from each zone can be derived.

As depicted in FIG. 1C, the fluids 24, 26 flowing into the wellbore 20 from the two lower zones 14, 16 each experience a Joule-Thompson cooling effect due to essentially dry gas being produced. The fluid 22 flowing into the wellbore 20 from the uppermost zone 12 experiences a Joule-Thomson heating effect, due to the production of two phase fluid.

These effects are readily observed in FIG. 1C. However, when there are a large number of zones, and fluid produced from those zones are comingled, the temperature difference at the fluid entries into a wellbore becomes smaller, increasing the uncertainty of the results of the flow rate analysis.

In FIG. 1D, a graph of pressure versus depth is representatively illustrated. In the FIG. 1D graph, the vertical axis represents depth along the wellbore 20 (with depth increasing in a downward direction), and the horizontal axis represents pressure (with pressure increasing to the right).

The curve P represents pressure in the wellbore 20. $P_1$, $P_2$ and $P_3$ indicate pressures in the zones 16, 14, 12, respectively. $\Delta P_1$, $\Delta P_2$ and $\Delta P_2$ indicate the pressure differences between the wellbore 20 and the respective zones 16, 14, 12 at the locations where the fluids 26, 24, 22 enter the wellbore.

Referring additionally now to FIG. 2A, another configuration of the well system 10 is representatively illustrated. The well system 10 of FIG. 2A is similar in many respects to the well system of FIG. 1A, but in the system of FIG. 2A another tubular string 34 (such as a velocity string or production tubing, etc.) is installed in the tubular string 18 for producing comingled fluids 22, 24, 26 from the well.

The optical waveguide 28 is installed adjacent the tubular string 34 (for example, clamped to an exterior of the tubular string), and measures temperature in an annulus 36 formed radially between the tubular strings 18, 34. In other examples, the optical waveguide 28 could be installed in an interior flow passage 38 of the tubular string 34, in a sidewall of the tubular string, or otherwise disposed in the well.

Preferably, the optical waveguide 28 is thermally isolated from the tubular string 34 itself, so that the DTS measurements are representative of the temperature of fluids 22, 24, 26 in the annulus 36, rather than the temperature of the tubular string. For example, the tubular string 34 might be vacuum insulated tubing, or insulated from the optical waveguide 28 in another way.

In the configuration of FIG. 2A, produced fluid flow (in this case, primarily gas) is bi-directional, flowing in via the perforations 32, downward through the annulus 36 to a lower end of the tubular string 34, and then upward through the tubular string to the surface.

Note that, as depicted in FIG. 2B, the flow rates $Q_1, Q_2, Q_3$ and fluid proportions from the respective zones 16, 14, 12 are the same as illustrated in FIG. 1B. However, the temperature $T_{DTS}$ as measured by the DTS system is substantially different (compare FIG. 2C to FIG. 1C).

One reason for this difference is that the fluids 22, 24, 26 are comingled in an opposite order in the system 10 of FIG. 2A as compared to the order in which the fluids are comingled in the system of FIG. 1A. Thus, although the Joule-Thomson effect $\Delta T_{JT}$, may be substantially the same for each of the fluids 22, 24, 26 in the FIGS. 1A & 2A configurations, the temperature $T_{DTS}$ measurements of the DTS system are substantially different.

FIG. 3A depicts the same well system 10 configuration as in FIG. 2A, except that the fluids 22, 24, 26 are produced to the surface via the annulus 36, instead of via the tubular string 34. The relative flow rates $Q_1, Q_2, Q_3$ and fluid proportions from the respective zones 16, 14, 12 are the same (as depicted in FIGS. 2B & 3B).

However, the upward flow of the fluids 22, 24, 26 through the annulus 36 results in a substantially different temperature measurement by the DTS system (compare FIGS. 2C & 3C). Indeed, the DTS temperature measurement $T_{DTS}$ of FIG. 3C is instead substantially the same as the DTS temperature measurement of FIG. 1C.

In a flow measurement method associated with the well system 10, the change between production of the fluids 22, 24, 26 via the tubular string flow passage 38, and production via the annulus 36, may be only temporary, and may be maintained for only a sufficient time to assure a substantially steady state response of the DTS system. Of course, long term production via the annulus 36 may be desirable in certain circumstances.

In FIG. 4B, the DTS temperature measurements for down annulus 36/up passage 38 flow ($T_{DTS2}$, as in the configuration of FIG. 2A) and up annulus 36 flow ($T_{DTS3}$, as in the configuration of FIG. 3A) are compared. Note that the difference in temperature measurement between the two configurations is primarily a result of the differences in the comingled fluids at each of the zones 12, 14, 16.

For example, at the upper zone 12, when the fluids 22, 24, 26 are flowed up the annulus 36 (as in the configuration of FIG. 3A), the fluid 22 is mixed with all of the fluids 24, 26 from the zones 14, 16 below. However, when the fluids 22, 24, 26 are flowed down the annulus 36 (as in the configuration of FIG. 3A), and up the passage 38, the fluid 22 from the upper zone 12 is not mixed with the fluids 24, 26 from the zones below 14, 16 until the fluid 22 arrives at the next lower zone 14.

Conversely, at the lower zone 16, when the fluids 22, 24, 26 are flowed up the annulus 36 (as in the configuration of FIG. 3A), the fluid 26 from the lower zone 16 is not mixed with the fluids 22, 24 from the zones above 12, 14 until the fluid 26 arrives at the next higher zone 14. However, when the fluids 22, 24, 26 are flowed down the annulus 36 (as in the configuration of FIG. 3A), and up the passage 38, the fluid 26 is mixed with all of the fluids 22, 24 from the zones 12, 14 above.

It will be appreciated that the characteristics of the fluid 22 can be more readily determined when DTS temperature measurements are made without the fluid 22 being comingled with the other fluids 24, 26. Likewise, the characteristics of the fluid 26 can be more readily determined when DTS temperature measurements are made without the fluid 26 being comingled with the other fluids 22, 24. In addition, once the characteristics of the fluids 22, 26 are accurately known, the characteristics of the fluid 24 can be more accurately determined.

By taking the DTS measurements during down annulus 36/up passage 38 flow, and then again during up annulus 36 flow, the difference between the two temperature curves can be used to obtain more accurate data with regard to the flow rates of oil, water and gas from each zone 12, 14, 16, thereby overcoming the limitations of taking DTS temperature measurements with only one direction of flow. This analysis methodology may be incorporated into flow analysis software (such as the iFlow™ software package provided by Halliburton Energy Services, Inc. of Houston, Tex. USA).

It may now be fully appreciated that the above disclosure provides valuable advancements to the art of fluid flow rate analysis in wells. Previous flow rate analyses from DTS temperature measurements have not considered comparing temperature measurements during opposite flow directions to make more accurate analysis of flow being produced from each zone.

More accurate analysis of fluid flow from each zone 12, 14, 16 can be made, using the principles of this disclosure, without adding cost. This is a desirable benefit, not available with use of prior methods.

Although only three zones 12, 14, 16 are described above, it will be appreciated that any number of zones may be intersected by the wellbore 20. Fluid from the zones may all be comingled in the wellbore 20, only selected ones of the fluids may be comingled, and any or all of the zones may be isolated from each other in the wellbore (e.g., using packers to seal off the annulus 36 between the zones). If zones are isolated from each other, then the commingling of fluids may take place in the passage 38 in the tubular string 34, in which case it may be advantageous to position the optical waveguide 28 so that it detects temperature of the fluids in the passage.

The above disclosure provides to the art a well system 10 and a method of determining characteristics of fluids 22, 24, 26 flowed between a wellbore 20 and multiple zones 12, 14, 16 intersected by the wellbore 20. The method includes: measuring a first distributed temperature $T_{DTS2}$ profile of the fluids 22, 24, 26 along the wellbore 20 while the fluids 22, 24, 26 flow in a first direction through the wellbore 20; and measuring a second distributed temperature $T_{DTS3}$ profile of the fluids 22, 24, 26 along the wellbore 20 while the fluids 22, 24, 26 flow in a second direction through the wellbore 20. The second direction is opposite to the first direction.

The method can include determining the characteristics of the fluids 22, 24, 26 based on a difference between the first and second distributed temperature profiles $T_{DTS2}$, $T_{DTS3}$.

The fluids 22, 24, 26 may flow in the first direction through an annulus 36 formed between tubular strings 18, 34 in the wellbore 20, during the first distributed temperature $T_{DTS2}$ profile measuring step.

The fluids 22, 24, 26 may flow in the second direction through a flow passage 38 extending longitudinally through an inner one of the tubular strings 34, during the first distributed temperature $T_{DTS2}$ profile measuring step.

The fluids 22, 24, 26 may flow in the second direction through the annulus 36, during the second distributed temperature $T_{DTS3}$ profile measuring step.

The first and second distributed temperature $T_{DTS2}$, $T_{DTS3}$ profile measuring steps may be performed using an optical waveguide 28 attached to a tubular string 34 in the wellbore. The optical waveguide 28 may be thermally insulated from the tubular string 34. The optical waveguide 28 may detect the temperature of the fluids 22, 24, 26 in an annulus 36 surrounding the tubular string 34.

A first one of the fluids 22 may flow through the wellbore 20 without being comingled with the other fluids 24, 26 in the first distributed temperature $T_{DTS2}$ profile measuring step, but the first fluid 22 may be immediately comingled with the other fluids 24, 26 upon flowing into the wellbore 20 in the second distributed temperature $T_{DTS3}$ profile measuring step.

A second one of the fluids 26 may flow through the wellbore 20 without being comingled with the other fluids 22, 24 in the second distributed temperature profile $T_{DTS3}$ measuring step, but the second fluid 26 may be immediately comingled with the other fluids 22, 24 upon flowing into the wellbore 20 in the first distributed temperature $T_{DTS2}$ profile measuring step.

Also described by the above disclosure is a method of determining characteristics of fluids 22, 24, 26 flowed between a wellbore 20 and multiple zones 12, 14, 16 intersected by the wellbore 20, in which the method includes the steps of: flowing the fluids 22, 24, 26 in a first direction through an annulus 36 formed between first and second tubular strings 18, 34 in the wellbore 20; measuring a first distributed temperature $T_{DTS2}$ profile of the fluids 22, 24, 26 during the step of flowing the fluids in the first direction; flowing the fluids 22, 24, 26 in a second direction through the annulus 36, the second direction being opposite to the first direction; and measuring a second distributed temperature $T_{DTS3}$ profile of the fluids 22, 24, 26 along the wellbore 20 during the step of flowing the fluids 22, 24, 26 in the second direction.

It is to be understood that the various embodiments of the present disclosure described herein may be utilized in various orientations, such as inclined, inverted, horizontal, vertical, etc., and in various configurations, without departing from the principles of the present disclosure. The embodiments are described merely as examples of useful applications of the principles of the disclosure, which is not limited to any specific details of these embodiments.

In the above description of the representative embodiments of the disclosure, directional terms, such as "above", "below", "upper", "lower", etc., are used for convenience in referring to the accompanying drawings. In general, "above", "upper", "upward" and similar terms refer to a direction toward the earth's surface along a wellbore, and "below", "lower", "downward" and similar terms refer to a direction away from the earth's surface along the wellbore.

Of course, a person skilled in the art would, upon a careful consideration of the above description of representative embodiments of the disclosure, readily appreciate that many modifications, additions, substitutions, deletions, and other changes may be made to the specific embodiments, and such changes are contemplated by the principles of the present disclosure. Accordingly, the foregoing detailed description is to be clearly understood as being given by way of illustration and example only, the spirit and scope of the present invention being limited solely by the appended claims and their equivalents.

What is claimed is:

1. A method of determining characteristics of fluids flowed between a wellbore and multiple zones intersected by the wellbore, the method comprising:
    measuring a first distributed temperature profile of the fluids along the wellbore while the fluids flow in a first direction through the wellbore; and
    measuring a second distributed temperature profile of the fluids along the wellbore while the fluids flow in a second direction through the wellbore, the second direction being opposite to the first direction, wherein the first and second distributed temperature profile measurings are performed using an optical waveguide attached to a first tubular string in the wellbore, and wherein the optical waveguide is thermally insulated from the first tubular string.

2. The method of claim 1, further comprising determining the characteristics of the fluids based on a difference between the first and second distributed temperature profiles.

3. The method of claim 1, wherein the fluids flow in the first direction through an annulus formed between the first tubular string and a second tubular string in the wellbore, during the first distributed temperature profile measuring.

4. The method of claim 3, wherein the fluids flow in the second direction through a flow passage extending longitudinally through an inner one of the first and second tubular strings, during the first distributed temperature profile measuring.

5. The method of claim 3, wherein the fluids flow in the second direction through the annulus, during the second distributed temperature profile measuring.

6. The method of claim 1, wherein the optical waveguide detects the temperature of the fluids in an annulus surrounding the first tubular string.

7. A method of determining characteristics of fluids flowed between a wellbore and multiple zones intersected by the wellbore, the method comprising:
    measuring a first distributed temperature profile of the fluids along the wellbore while the fluids flow in a first direction through the wellbore; and
    measuring a second distributed temperature profile of the fluids along the wellbore while the fluids flow in a second direction through the wellbore, the second direction being opposite to the first direction, wherein a first one of the fluids flows through the wellbore without being commingled with the other fluids in the first distributed temperature profile measuring, but the first fluid is immediately commingled with the other fluids upon flowing into the wellbore in the second distributed temperature profile measuring.

8. The method of claim 7, wherein a second one of the fluids flows through the wellbore without being commingled with the other fluids in the second distributed temperature profile measuring, but the second fluid is immediately commingled with the other fluids upon flowing into the wellbore in the first distributed temperature profile measuring.

9. A method of determining characteristics of fluids flowed between a wellbore and multiple zones intersected by the wellbore, the method comprising:

flowing the fluids in a first direction through an annulus formed between first and second tubular strings in the wellbore;

measuring a first distributed temperature profile of the fluids along the wellbore during the flowing of the fluids in the first direction;

flowing the fluids in a second direction through the annulus, the second direction being opposite to the first direction; and measuring a second distributed temperature profile of the fluids along the wellbore during the flowing of the fluids in the second direction.

10. The method of claim 9, further comprising determining the characteristics of the fluids based on a difference between the first and second distributed temperature profiles.

11. The method of claim 9, wherein the fluids flow in the second direction through a flow passage extending longitudinally through the second tubular string, during the first distributed temperature profile measuring.

12. The method of claim 9, wherein the first and second distributed temperature profile measurings are performed using an optical waveguide attached to the second tubular string.

13. The method of claim 12, wherein the optical waveguide is thermally insulated from the second tubular string.

14. The method of claim 12, wherein the optical waveguide detects the temperature of the fluids in the annulus surrounding the second tubular string.

15. A method of determining characteristics of fluids flowed between a wellbore and multiple zones intersected by the wellbore, the method comprising:

flowing the fluids in a first direction through an annulus formed between first and second tubular strings in the wellbore;

measuring a first distributed temperature profile of the fluids during flowing the fluids in the first direction;

flowing the fluids in a second direction through the annulus, the second direction being opposite to the first direction; and measuring a second distributed temperature profile of the fluids along the wellbore during flowing the fluids in the second direction, wherein a first one of the fluids flows through the annulus without being commingled with the other fluids in the first distributed temperature profile measuring, but the first fluid is immediately commingled with the other fluids upon flowing into the annulus in the second distributed temperature profile measuring.

16. The method of claim 15, wherein a second one of the fluids flows through the annulus without being commingled with the other fluids in the second distributed temperature profile measuring, but the second fluid is immediately commingled with the other fluids upon flowing into the annulus in the first distributed temperature profile measuring.

* * * * *